United States Patent [19]

Kobayashi et al.

[11] Patent Number: 4,780,477

[45] Date of Patent: Oct. 25, 1988

[54] ISATIN COMPOSITIONS HAVING ANTI-ULCER ACTIVITIES

[75] Inventors: Michihiro Kobayashi, Akashina; Makio Kitazawa, Matsumoto; Masuo Akahane, Matsumoto; Tsutomu Tsukamoto, Matsumoto; Ryoji Yamamoto, Matsumoto; Yasushi Nakano, Shiojiri, all of Japan

[73] Assignee: Kissei Pharmaceutical Co., Ltd., Matsumoto, Japan

[21] Appl. No.: 868,146

[22] Filed: May 29, 1986

[30] Foreign Application Priority Data

Aug. 6, 1985 [JP] Japan .................................. 60-124919

[51] Int. Cl.[4] ..................... A61K 31/40; C07D 209/34
[52] U.S. Cl. .................................. 514/418; 548/484; 548/485; 548/486
[58] Field of Search ....................... 548/484, 485, 486; 514/418

[56] References Cited

U.S. PATENT DOCUMENTS

| | | | |
|---|---|---|---|
| 3,374,234 | 3/1968 | Arya | 548/485 |
| 3,558,646 | 1/1971 | Bruderlein | 548/485 |
| 3,631,063 | 12/1971 | Lednicer | 548/484 |
| 4,374,846 | 2/1983 | Heinemann | 548/484 |

OTHER PUBLICATIONS

Daunis et al, Bull. Soc. Chim. Fr., vol. 6, (1970), pp. 2289-2291.

*Primary Examiner*—Donald G. Daus
*Assistant Examiner*—Mark W. Noel
*Attorney, Agent, or Firm*—Depaoli & O'Brien

[57] ABSTRACT

This invention provides novel isatin compounds which are useful as therapeutic agents. The invention isatin compounds and the pharmaceutically acceptable salts thereof exhibit anti-ulcer activities which are applicable for propylaxis and treatment of ulcer diseases in the digestive tract of animals.

11 Claims, No Drawings

ISATIN COMPOSITIONS HAVING ANTI-ULCER ACTIVITIES

FIELD OF THE INVENTION

This invention relates to novel isatin compounds and pharmaceutically acceptable salts thereof. More particularly, this invention relates to isatin compounds and pharmaceutically acceptable salts thereof having anti-ulcer activities for prophylaxis and treatment of ulcer diseases, to a method for prophylaxis and treatment of ulcer diseases using said isatin compounds or pharmaceutically acceptable salts, and to a pharmaceutical composition for prophylaxis and treatment of ulcer diseases containing one of the said isatin compounds or pharmaceutically acceptable salts thereof as active ingredients.

BACKGROUND OF THE INVENTION

In recent years, the accepted treatment for ulcer diseases in the digestive tract has depended upon drugs such as antacids which neutralize gastric acid, anticholinergics and histamine $H_2$-receptor antagonists which reduce acid secretion in the stomach, and a drug such as sucralfate which increases the rate of healing of ulcer diseases but does not inhibit gastric acid secretion. The latter compound may have cytoprotective (mucoprotective) effects similar to the prostaglandins and prostaglandin analogs.

However, in stomach and duodenum ulcer diseases induced by stress, which are on increase in recent years, a breakdown of the defensive system of the gastric and duodenal tract can be frequently observed.

As a result of extensive studies of the type of compounds which are useful for prophylaxis and treatment of restraint and water-immersion stress ulcers, it was found that the novel isatin compounds of this invention exhibit anti-ulcer activities which are useful for prophylaxis of stress-induced ulcers caused by restraint and water-immersion in Wister strain rats.

Furthermore, the isatin compounds of this invention have curing effects for acetic acid-induced ulcer diseases, and thus are useful for treatment of chronic ulcer diseases.

The isatin compounds of this invention have prophylactic effects for hydrochloric acid or ethanol-induced gastric mucosal lesions. These findings demonstrate that the isatin compounds of this invention have cytoprotective activities and are useful for prophylaxis and treatment of ulcer diseases.

The isatin compounds of this invention inhibit gastric acid secretion induced by administrating 2-deoxy-D-glucose but do not inhibit gastric acid secretion induced by administrating histamine, carbachol or pentagastrin. These results demonstrate that the novel isatin compounds have gastric acid secretion activities due to certain central nervous system activities. However, the isatin compounds of this invention do not prolong sleeping time or exhibit an inhibition of motor activities.

Isatin 3-semicarbazone derivatives such as isatin 3-semicarbazone, 1-methylisatin 3-semicarbazone, 1-benzylisatin 3-semicarbazone and isatin 3-(4-aminoalkyl-semicarbazones) are disclosed in Chem. Rev., Vol. 34, 393 (1944), Chem. Abstr., Vol. 43, 8979g (1949), Chem. Abstr., Vol. 45, 8005g (1951), Chem. Abstr., Vol. 47, 5542f (1953), Chem. Abstr., Vol. 73, 76977b (1970) and Chem. Abstr., Vol. 77, 152122u (1972). However, these reference articles do not indicate any pharmacological effects associated with these disclosed isatin 3-semicarbazone derivatives.

On the other hand, with regard to 1-dialkylaminoalkylisatin 3-thiosemicarbazones, many compounds are disclosed in U.S. Pat. No. 3,374,234, Sci. Pharm., Vol. 38, 98 (1970), J. Med. Chem., Vol. 10, 972 (1967), J. Pharm. Sci., Vol. 68, 459 (1979), Arzneim. Forsch., Vol. 30, 1839 (1980) and Chim. Ther., Vol. 8, 447 (1973). These reference articles disclose that these compounds have pharmacological effects such as antiviral, antibacterial or antifungal effect, and are useful as therapeutic agents.

Specifically, U.S. Pat. No. 3,374,234 above discloses isatin 3-thiosemicarbazones represented by the general formula:

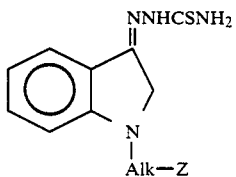

wherein Alk represents an alkylene group having 1 to 5 carbon atoms and Z represents an amino group, and indicates that these compounds have pharmacological effects such as antiviral, antibacterial, central stimulating, antihistaminic or analgesic agents, and are useful for therapeutic agents.

With regard to the physical properties of isatin 3-semicarbazones and isatin 3-thiosemicarbazones, Thompson et al. have reported in Chem. Abstr., Vol. 47, 5542f (1953) that antiviral activities of isatin 3-thiosemicarbazones are not found in isatin 3-semicarbazones. Furthermore, Tomchin et al. have reported in Chem. Abstr., Vol. 79, 41782f, 91459b (1973) and Vol. 81, 37145z (1974) that isatin 3-thiosemicarbazones exist predominantly in the Z-form and isatin 3-semicarbazones are mainly in the E-form and that the isatin 3-semicarbazones in the E-form can be isomerized to the Z-form by heating or treating with an acid. These facts demonstrate that isatin 3-semicarbazones and isatin 3-thiosemicarbazones exhibit different physical properties.

SUMMARY OF THE INVENTION

An object of this invention is to provide novel isatin compounds and pharmaceutically acceptable salts thereof having anti-ulcer activities.

Another object of this invention is to provide a method for prophylaxis and treatment of ulcer diseases in the digestive tract or mammals using said isatin compounds and pharmaceutically acceptable salts thereof.

A further object of this invention is to provide a pharmaceutical composition for prophylaxis and treatment of ulcer diseases containing one of the said isatin compounds or pharmaceutically acceptable salts thereof as an active ingredient.

Other objects, features and advantages of this invention will be apparent from the following description of the invention.

This invention provides novel isatin compounds corresponding to the formula:

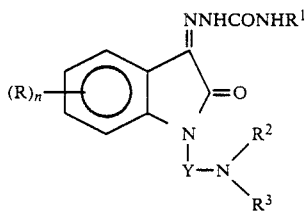

where $R_1$ is hydrogen or an alkyl, aryl, aralkyl, or cycloalkyl group, $R_2$ is a branched-chain alkyl group, $R_3$ is hydrogen or an alkyl, aralkyl, or cycloalkyl group, R is halogen or an alkyl, alkoxy, amino, acylamino, or alkoxycarbonyl group, n is an integer of 0–2, and Y is an alkylene group; and pharmaceutically acceptable salts thereof.

The term "alkyl" as used herein means a straight- or branched-chain alkyl group having 1 to 6 carbon atoms.

The term "aralkyl" as used herein means an aralkyl group having 7 to 10 carbon atoms.

The term "cycloalkyl" as used herein means a cycloalkyl group having 3 to 6 carbon atoms.

The term "branched-chain alkyl" as used herein means a branched-chain alkyl group having 3 to 6 carbon atoms.

The term "alkoxycarbonyl" as used herein means an alkoxycarbonyl group having 2 to 7 carbon atoms.

The term "acylamino" as used herein means an acylamino group having 1 to 5 carbon atoms.

The term "alkylene" as used herein means a straight- or branched-chain alkylene group having 2 to 4 carbon atoms.

DETAILED DESCRIPTION OF THE INVENTION

Novel isatin compounds and pharmaceutically acceptable salts thereof of this invention possess anti-ulcer activities and are useful as propylactic and treating agents for ulcer diseases in the digestive tract, such as ulcer diseases in the stomach and the duodenum of mammals.

The isatin compounds represented by the general formula (I) of the present invention can be prepared in accordance with known procedures. A general method for synthesizing isatin compounds of this invention corresponding to the general formula (I):

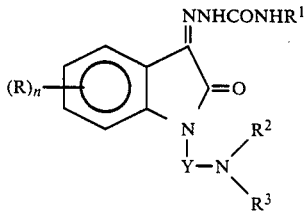

involves reacting a compound represented by the general formula (II):

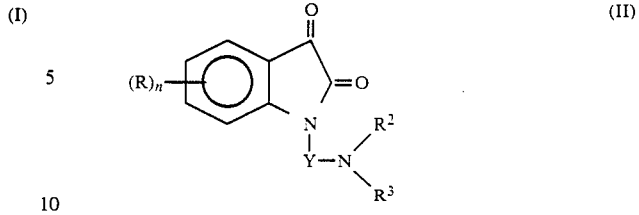

where R, $R^2$, $R^3$, n and Y are as previously defined, with a semicarbazide derivative represented by the general formula (III):

$$H_2NNHCONHR^1 \quad (III)$$

where $R^1$ is as previously defined, or with its acid salt.

Isatin compounds represented by the general formula (I) of this invention, where $R^1$ is an alkyl, aryl, aralkyl or cycloalkyl group, can be prepared also by reacting a present invention compound having an $R^1$ hydrogen atom with an amino compound represented by the general formula (IV):

$$NH_2R^4 \quad (IV)$$

where $R^4$ represents an alkyl, aryl, aralkyl or a cycloalkyl group.

The reaction of a compound represented by the general formula (II) with a semicarbazide compound represented by the general formula (III) or its acid salt can be accomplished in accordance with the following procedure.

A compound of the general formula (II) is dissolved in an inert organic solvent such as aqueous alcohol, and to the solution is added a semicarbazide compound of the general formula (III) or its acid salt in an equimolar amount or in a slight excess amount relative to the compound of the general formula (II), and then, if required sodium acetate, acetic acid or hydrochloric acid is added to the reaction mixture. The reaction is conducted for a period of about 1–40 hours at a temperature of about 0°–80° C. After completion of the reaction, a precipitate is formed by concentrating of the reaction mixture under reduced pressure, or by adding an aqueous basic solution such as an aqueous sodium bicarbonate solution or an aqueous sodium hydroxide solution to the residue after concentration of the reaction mixture. The precipitate is collected by filtration, and purified with silica gel column chromatography and/or recrystallized from an adequate solvent to provide an isatin compound of the general formula (I).

The compounds represented by the general formula (II) employed as starting materials of this invention can be prepared by reacting a compound corresponding to the general formula (V):

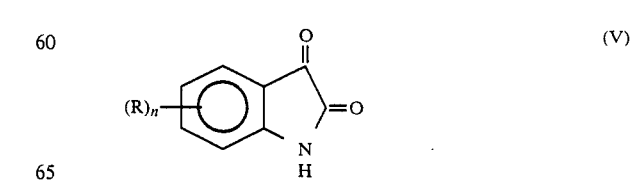

where R and n are as previously defined, with a compound corresponding to the general formula (VI):

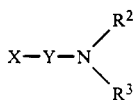

(VI)

where X is an acid residual group such as halogen, and $R^2$, $R^3$ and Y defined; or by reacting compound (V) with the corresponding acid salt of compound (VI).

Alternatively, the compound represented by the general formula (II) can be prepared by reacting a compound corresponding to the general formula (VII):

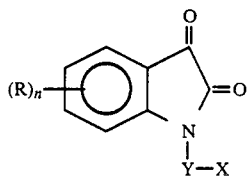

(VII)

where R, n, X and Y are as previously defined, with an amino compound corresponding to the general formula (VIII):

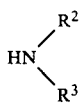

(VIII)

where $R^2$ and $R^3$ are as previously defined, above, and said amine is employed in an equimolar amount or an excess amount to the compound of the general formula (VII) in the usual manner.

Some of the compounds of the general formulae (III), (IV), (V), (VI), (VII) and (VIII) are known compounds, and can be purchased or can be prepared by methods described in the literature.

The isatin compounds represented by the general formula (I) can be converted into pharmaceutically acceptable salts by conventional means. For example, a hydrochloric acid salt can be prepared by dissolving an isatin compound of general formula (I) in methanol, adding to the solution a 1N hydrochloric acid in an equimolar amount or a slight excess amount relative to the isatin compound, concentrating the reaction mixture, adding diethyl ether to the residue to form a precipitate, collecting the precipitates by filtration, and then recrystallizing the precipitates from a suitable solvent. Examples of such pharmaceutically acceptable salts include pharmaceutically acceptable inorganic or organic acid salts such as a sulfuric acid salt, a p-toluenesulfonic acid salt, an acetic acid salt, a citric acid salt, a tartaric acid salt, a malic acid salt, a fumaric acid salt, and the like. These salts have anti-ulcer effects as high as the corresponding formula (I) compounds having a free amino group.

The isatin compounds of the general formula (I) and the pharmaceutically acceptable salts thereof possess strong anti-ulcer activities for prophylaxis and treatment of ulcer diseases in some experimental ulcer diseases, i.e., restraint and water-immersion stress-induced, acetic acid-induced and aspirin-induced ulcers in animals, and ethanol-induced and hydrochloric acid-induced mucosal lesions in animals. For example, these isatin compounds are effective for reducing the restraint and water-immersion stress-induced ulcer to a degree between about 40-95% as compared with a control, as determined by the length of the ulcer at a dose of 100 mg per kg of body weight by oral administration.

Also, the anti-ulcer activities of the isatin compounds of this invention at a dose of 100 mg/kg, e.g., (E)-1-(2-diisopropylaminoethyl)isatin 3-semicarbazone, is approximately equivalent to that of cimetidine at a dose of 100 mg/kg in acetic acid-induced ulcer by oral administration.

The isatin compounds of the general formula (I) and the pharmaceutically acceptable salts have two geometrical isomers, i.e., E-form and Z-form, which can be employed individually or as a mixture in the practice of the present invention.

Preferred isatin compounds of the general formula (I) of this invention include (E)-1-(2-diisopropylaminoethyl)isatin 3-semicarbazone, (E)-1-(2-diisopropylaminoethyl)isatin 3-(4-methylsemicarbazone), (E)-1-(2-diisopropylaminoethyl)isatin 3-(4-benzylsemicarbazone), (E)-1-(2-diisopropylaminoethyl)isatin 3-(4-cyclohexylsemicarbazone), (E)-1-(2-diisopropylaminoethyl)-5-fluoroisatin 3-semicarbazone, (E)-5-chloro-1-(2-diisopropylaminoethyl)isatin 3-semicarbazone, (E)-5-bromo-1-(2-diisopropylaminoethyl)isatin 3-semicarbazone, (E)-1-(2-diisopropylaminoethyl)-5-methylisatin 3-semicarbazone, (Z)-1-(2-diisopropylaminoethyl)- 7-methoxycarbonylisatin 3-semicarbazone, (E)-1-[2-(N-isopropylcyclohexylamino)ethyl]isatin 3-semicarbazone and the corresponding acid salts. A particularly preferred compound is (E)-1-(2-diisopropylaminoethyl)isatin 3-semicarbazone.

The isatin compounds of formula (I) and the pharmaceutically acceptable salts thereof can be administered to humans and other mammalia by oral, intravenous, intramuscular, or intrarectal administration, and for administration the isatin compounds can be formulated into pharmaceutical compositions together with conventional pharmaceutically acceptable carriers or excipients.

The isatin compounds and the pharmaceutically acceptable salts of formula (I) can be administered in various dosage forms depending upon the intended therapy. Typical dosage forms which can be utilized are tablets, pills, powders, liquid preparations, suspensions, emulsions, granules, capsules, suppositories, and injections.

For molding a pharmaceutical composition into tablet form, a wide variety of conventional carriers known in the art can be used. Examples of suitable carriers are excipients such as glucose, lactose, starch, cacao butter, hardened vegetable oils, kaolin and talc, binders such as gum arabic powder, tragacanth powder, and ethanol, and disintegrants such as laminaria and agar. If desired the tablets can be coated with one or more layers of sugar or gelatin or other type of coating.

When a pharmaceutical composition is formulated into an injectable preparation, it is preferred that the resulting injectable solution and suspension are sterilized and rendered isotonic with respect to blood. In formulating a pharmaceutical composition in the form of a solution or suspension, any diluent customarily used in the art can be employed. Examples of suitable diluents include water, ethyl alcohol, propylene glycol, polyoxyethylene sorbitol and sorbitan esters, and the like. Sodium chloride, glucose or glycerol may be incorporated into a liquid preparation in an amount sufficient to prepare an isotonic solution.

The therapeutic agent may further contain ordinary dissolving aids, buffers, pain-alleviating agents, and preservatives, and optionally, coloring agents, fragrances, flavors, sweeteners, and other pharmacologically active agents which are known in the art.

The dosage of an isatin compound of this invention can be in a range of about 10–5,000 mg per adult human per day by oral administration, or about 1–1000 mg per adult human per day by parenteral administration, in multiple doses depending upon the type of disease, the severity of condition to be treated, and the like.

This invention is further illustrated in more detail by way of the following reference examples and examples. The melting point of the products obtained is uncorrected.

REFERENCE EXAMPLE 1

1-(2-Diisopropylaminoethyl)isatin 2.94 Grams of isatin and 4.00 g of 2-diisopropylaminoethyl chloride hydrochloride were suspended in a mixture of 50 ml of dry toluene and 10 ml of dry N,N-dimethylformamide, and 1.60 g of sodium hydride (60% dispersion in mineral oil) was added to the suspension with stirring under ice-cooling. The mixture was stirred for 30 minutes at room temperature, and then heated at 80° C. for 19 hours. The reaction mixture was concentrated under reduced pressure, and water was added to the residue. The mixture was extracted with benzene, and the benzene layer was washed with water, dried over anhydrous magnesium sulfate and concentrated under reduced pressure. The residue was recrystallized from hexane to obtain 4.62 g of 1-(2-diisopropylaminoethyl)isatin having a melting point of 60°–61° C.

| Elemental analysis as $C_{16}H_{22}N_2O_2$ | | | |
|---|---|---|---|
| | C % | H % | N % |
| Calcd. | 70.04 | 8.08 | 10.21 |
| Found | 69.99 | 8.29 | 10.06 |

IR (KBr): $\nu$co 1725 cm$^{-1}$.

NMR (CDCl$_3$) δ: 0.98(12H, d, J=6.6 Hz), 2.70(2H, t, J=6.9 Hz), 3.04(2H, sept, J=6.6 Hz), 3.69(2H, t, J=6.9 Hz), 6.91(1H, d, J=7.2 Hz), 7.09(1H, t, J=7.2Hz), 7.57(1H, t, J=7.2 Hz), 7.59(1H, d, J=7.2Hz).

REFERENCE EXAMPLE 2

1-(2-Diisopropylaminoethyl)isatin

A suspension of 2.94 g of isatin, 4.20 g of 2-diisopropylaminoethyl chloride hydrochloride, and 3.17 g of anhydrous potassium carbonate in 50 ml of toluene was stirred for 4 hours at 90° C. After cooling, the reaction mixture was washed with water, dried over anhydrous magnesium sulfate and concentrated under reduced pressure. The residue was recrystallized from hexane to obtain 4.93 g of 1-(2-diisopropylaminoethyl)isatin. The chemical properties of this product are identical with those of the product obtained by Reference Example 1.

REFERENCE EXAMPLE 3

1-(3-Diisopropylaminopropyl)isatin

By using isatin and 3-diisopropylaminopropyl chloride hydrochloride, a method analogous to that described in Reference Example 1 was carried out, and the reaction product was purified with silica gel column chromatography (eluent: chloroform/methanol=50/1) and then recrystallized from hexane to obtain 1-(3-diisopropylaminopropyl)isatin having a melting point of 49°–50° C. (yield: 72.9%).

| Elemental analysis as $C_{17}H_{24}N_2O_2$ | | | |
|---|---|---|---|
| | C % | H % | N % |
| Calcd. | 70.80 | 8.39 | 9.71 |
| Found | 70.98 | 8.35 | 9.41 |

IR (KBr): $\nu$co 1720 cm$^{-1}$.

NMR (CDCl$_3$) δ: 1.02(12H, d, J=6.6 Hz), 1.79(2H, quint, J=6.6 Hz), 2.55(2H, t, J=6.6 Hz), 3.04(2H, sept, J=6.6 Hz), 3.76(2H, t, J=6.6 Hz), 6.93(1H, d, J=7.7 Hz), 7.10(1H, t, J=7.7 Hz), 7.58(1H, t, J=7.7 Hz), 7.60(1H, d, J=7.7 Hz).

REFERENCE EXAMPLE 4

1-(2-Diisopropylaminopropyl)isatin and
1-(2-diisopropylamino-1-methylethyl)isatin To a solution of 4.16 g of isatin and 6.06 g of 2-diisopropylamino-1-methylethyl chloride hydrochloride in 80 ml of dry N,N-dimethylformamide was added 2.28 g of sodium hydride (60% dispersion in mineral oil) with stirring under ice-cooling. The mixture was stirred for 30 minutes at room temperature and heated at 90° C. for 15 hours. The reaction mixture was concentrated under reduced pressure, and water was added to the residue. The mixture was extracted with ethyl acetate, and the ethyl acetate layer was washed with water, dried over anhydrous magnesium sulfate and concentrated under reduced pressure. The residue was triturated with hexane and the precipitates were collected by filtration. The crystals were recrystallized from benzene-hexane to obtain 4.48 g of 1-(2-diisopropylaminopropyl)isatin having a melting point of 111°–112° C.

| Elemental analysis as $C_{17}H_{24}N_2O_2$ | | | |
|---|---|---|---|
| | C % | H % | N % |
| Calcd. | 70.80 | 8.39 | 9.71 |
| Found | 70.86 | 8.59 | 9.65 |

IR (KBr): $\nu$co 1720 cm$^{-1}$.

NMR (CDCl$_3$) δ: 0.89(6H, d, J=6.6 Hz), 1.01(6H, d, J=6.6 Hz), 1.12(3H, d, J=6.6 Hz), 3.16(2H, sept, J=6.6 Hz), 3.3–3.45(1H, m), 3.46(1H, dd, J=6.6 and 13.7 Hz), 3.71(1H, dd, J=7.7 and 13.7 Hz), 6.87(1H, d, J=7.7 Hz), 7.09(1H, t, J=7.7 Hz), 7.55–7.65(2H, m).

On the other hand, the filtrate above was concentrated under reduced pressure, the residue was purified with silica gel column chromatography (eluent: chloroform) and then recrystallized from hexane to obtain 0.83 g of 1-(2-diisopropylamino-1-methylethyl)isatin having a melting point of 70°–71° C.

| Elemental analysis as $C_{17}H_{24}N_2O_2$ | | | |
|---|---|---|---|
| | C % | H % | N % |
| Calcd. | 70.80 | 8.39 | 9.71 |
| Found | 70.81 | 8.60 | 9.57 |

IR (KBr): $\nu$co 1730 cm$^{-1}$.

NMR (CDCl$_3$) δ: 0.82(6H, d, J=6.6 Hz), 0.96(6H, d, J=6.6 Hz), 1.50(3H, d, J=7.2 Hz), 2.68(1H, dd, J=5.3 and 14.0 Hz), 2.9–3.05(3H, m), 4.25–4.45(1H, m), 6.98(1H, d, J=7.7 Hz), 7.06(1H, t, J=7.7 Hz), 7.53(1H, dt, J=1.1 and 7.7 Hz), 7.58(1H, dd, J=1.1 and 7.7 Hz).

REFERENCE EXAMPLE 5

1-(2-Diisopropylaminoethyl)-5-methylisatin

A method analogous to that described in Reference Example 1 was carried out to obtain 1-(2-diisopropylaminoethyl)-5-methylisatin having a melting point of 65°–67° C. (yield: 82.0%) by using 5-methylisatin and 2-diisopropylaminoethyl chloride hydrochloride.

| | Elemental analysis as $C_{17}H_{24}N_2O_2$ | | |
|---|---|---|---|
| | C % | H % | N % |
| Calcd. | 70.80 | 8.39 | 9.71 |
| Found | 70.58 | 8.34 | 9.44 |

IR (KBr): $\nu co$ 1720 cm$^{-1}$.

NMR (CDCl$_3$) δ: 0.97(12H, d, J=6.6 Hz), 2.33(3H, s), 2.68(2H, t, J=6.6 Hz), 3.03(2H, sept, J=6.6 Hz), 3.67(2H, t, J=6.6 Hz), 6.80(1H, d, J=7.7 Hz), 7.38(1H, d, J=7.7 Hz), 7.39(1H, s).

REFERENCE EXAMPLE 6

1-(2-Diisopropylaminoethyl)-7-methylisatin

A method analogous to that described in Reference Example 1 was carried out to obtain 1-(2-diisopropylaminoethyl)-7-methylisatin having a melting point of 92°–93° C. (yield: 65.2%) by using 7-methylisatin and 2-diisopropylaminoethyl chloride hydrochloride.

| | Elemental analysis as $C_{17}H_{24}N_2O_2$ | | |
|---|---|---|---|
| | C % | H % | N % |
| Calcd. | 70.80 | 8.39 | 9.71 |
| Found | 70.62 | 8.49 | 9.66 |

IR (KBr): $\nu co$ 1720 cm$^{-1}$.

NMR (CDCl$_3$) δ: 0.93(12H, d, J=6.6 Hz), 2.53(3H, s), 2.68(2H, t, J=6.6 Hz), 3.03(2H, sept, J=6.6 Hz), 3.96(2H, t, J=6.6 Hz), 6.99(1H, t, J=7.1 Hz), 7.33(1H, d, J=7.1 Hz), 7.47(1H, d, J=7.1 Hz).

REFERENCE EXAMPLE 7

1-(2-Diisopropylaminoethyl)-5-fluoroisatin

To a suspension of 3.30 g of 5-fluoroisatin and 4.00 g of 2-diisopropylaminoethyl chloride hydrochloride in 75 ml of dry N,N-dimethylformamide was added 1.60 g of sodium hydride (60% dispersion in mineral oil) with stirring under ice-cooling. The mixture was stirred for 30 minutes at room temperature and then heated at 80° C. for 17 hours. The reaction mixture was concentrated under reduced pressure, and water was added to the residue. The mixture was extracted with benzene, and the benzene layer was washed with water, dried over anhydrous magnesium sulfate and concentrated under reduced pressure. The residue was recrystallized from hexane-petroleum benzine (boiling point range of 50°–80° C., and containing 60–70% hexane; distributed by Wako Pure Chemical Industries, LTD) to obtain 4.97 g of 1-(2-diisopropylaminoethyl)-5-fluoroisatin having a melting point of 100°–102° C.

| | Elemental analysis as $C_{16}H_{21}FN_2O_2$ | | |
|---|---|---|---|
| | C % | H % | N % |
| Calcd. | 65.73 | 7.24 | 9.58 |
| Found | 65.64 | 7.52 | 9.59 |

IR (KBr): $\nu co$ 1725 cm$^{-1}$.

NMR (CDCl$_3$) δ: 0.97(12H, d, J=6.6 Hz), 2.70(2H, t, J=6.6 Hz), 3.03(2H, sept, J=6.6 Hz), 3.69(2H, t, J=6.6 Hz), 6.85–6.95(1H, m), 7.25–7.4(2H, m).

REFERENCE EXAMPLE 8

5-Chloro-1-(2-diisopropylaminoethyl)isatin

A method analogous to that described in Reference Example 7 was carried out to obtain 5-chloro-1-(2-diisopropylaminoethyl)isatin having a melting point of 99°–101° C. (yield: 70.0%, recrystallizing solvent: hexane) by using 5-chloroisatin and 2-diisopropylaminoethyl chloride hydrochloride.

| | Elemental analysis as $C_{16}H_{21}ClN_2O_2$ | | |
|---|---|---|---|
| | C % | H % | N % |
| Calcd. | 62.23 | 6.85 | 9.07 |
| Found | 61.99 | 6.87 | 8.99 |

IR (KBr): $\nu co$ 1730 cm$^{-1}$.

NMR (CDCl$_3$) δ: 0.96(12H, d, J=6.6 Hz), 2.69(2H, t, J=6.6 Hz), 3.02(2H, sept, J=6.6 Hz), 3.69(2H, t, J=6.6 Hz), 6.89(1H, d, J=8.8 Hz), 7.5–7.6(2H, m).

REFERENCE EXAMPLE 9

6-Chloro-1-(2-diisopropylaminoethyl)isatin

A method analogous to that described in Reference Example 1 was carried out to obtain 6-chloro-1-(2-diisopropylaminoethyl)isatin having a melting point of 78°–79° C. (yield: 86.2%) by using 6-chloroisatin and 2-diisopropylaminoethyl chloride hydrochloride.

| | Elemental analysis as $C_{16}H_{21}ClN_2O_2$ | | |
|---|---|---|---|
| | C % | H % | N % |
| Calcd. | 62.23 | 6.85 | 9.07 |
| Found | 61.98 | 6.97 | 9.00 |

IR (KBr): $\nu co$ 1730 cm$^{-1}$.

NMR (CDCl$_3$) δ: 0.96(12H, d, J=6.6 Hz), 2.71(2H, t, J=6.6 Hz), 3.03(2H, sept, J=6.6 Hz), 3.68(2H, t, J=6.6 Hz), 6.95(1H, d, J=1.7 Hz), 7.06(1H, dd, J=1.7 and 8.2 Hz), 7.52(1H, d, J=8.2 Hz).

REFERENCE EXAMPLE 10

5-Bromo-1-(2-diisopropylaminoethyl)isatin

By using 5-bromoisatin and 2-diisopropylaminoethyl chloride hydrochloride, a method analogous to that described in Reference Example 7 was carried out to obtain 5-bromo-1-(2-diisopropylaminoethyl)isatin having a melting point of 91°–93° C. (yield: 82.9%).

| | Elemental analysis as $C_{16}H_{21}BrN_2O_2 \cdot 0.1C_6H_{14}$ (hexane) | | |
|---|---|---|---|
| | C % | H % | N % |
| Calcd. | 55.10 | 6.24 | 7.74 |
| Found | 55.25 | 6.32 | 7.70 |

IR (KBr): νco 1725 cm⁻¹.

NMR (CDCl₃) δ: 0.96(12H, d, J=6.6 Hz), 2.69(2H, t, J=6.6 Hz), 3.02(2H, sept, J=6.6 Hz), 3.68(2H, t, J=6.6 Hz), 6.8–6.85(1H, m), 7.65–7.7(2H, m).

REFERENCE EXAMPLE 11

5-Acetamido-1-(2-diisopropylaminoethyl)isatin

By using 5-acetamidoisatin and 2-diisopropylaminoethyl chloride hydrochloride, a method analogous to that described in Reference Example 7 was carried out to obtain 5-acetamido-1-(2-diisopropylaminoethyl)isatin having a melting point of 187°–190° C. (yield: 77.0%, recrystallizing solvent: ethyl acetate-hexane).

| | Elemental analysis as $C_{18}H_{25}N_3O_3$ | | |
|---|---|---|---|
| | C % | H % | N % |
| Calcd. | 65.24 | 7.60 | 12.68 |
| Found | 65.07 | 7.61 | 12.38 |

IR (KBr): νNH 3300 cm⁻¹ νco 1720, 1660 cm⁻¹.

NMR (d₆-DMSO) δ: 0.88(12H, d, J=6.6 Hz), 2.04(3H, s), 2.62(2H, t, J=6.6 Hz), 2.99(2H, sept, J=6.6 Hz), 3.62(2H, t, J=6.6 Hz), 7.10(1H, d, J=7.5 Hz), 7.72(1H, dd, J=2.2 and 7.5 Hz), 7.84(1H, d, J=2.2 Hz), 10.05(1H, s).

REFERENCE EXAMPLE 12

5-Amino-1-(2-diisopropylaminoethyl)isatin 2.07 Grams of 5-acetamido-1-(2-diisopropylaminoethyl)isatin was dissolved in 150 ml of a 6N-hydrochloric acid and the solution was heated under reflux for 1.5 hours. The reaction mixture was concentrated under reduced pressure, and an aqueous sodium bicarbonate solution was added to the residue. The mixture was extracted with chloroform, and the chloroform layer was washed with water, dried over anhydrous magnesium sulfate, and concentrated under reduced pressure. The residue was dissolved in ethyl acetate, and the solution was treated with an activated charcoal and concentrated under reduced pressure. The residue was recrystallized from ethyl acetate-hexane to obtain 1.45 g of 5-amino-1-(2-diisopropylaminoethyl)isatin having a melting point of 166°–167° C.

| | Elemental analysis as $C_{16}H_{23}N_3O_2$ | | |
|---|---|---|---|
| | C % | H % | N % |
| Calcd. | 66.41 | 8.01 | 14.52 |
| Found | 66.16 | 8.05 | 14.24 |

IR (KBr): νNH 3420, 3320 cm⁻¹ νco 1715 cm⁻¹.

NMR (d₆-DMSO) δ: 0.88(12H, d, J=6.6 Hz), 2.59(2H, t, J=6.6 Hz), 2.98(2H, sept, J=6.6 Hz), 3.55(2H, t, J=6.6 Hz), 5.13(2H, s), 6.76(1H, d, J=2.2 Hz), 6.84(1H, d, J=8.2 Hz), 6.89(1H, dd, J=2.2 and 8.2 Hz).

REFERENCE EXAMPLE 13

Methyl 1-(2-diisopropylaminoethyl)-7-isatincarboxylate

By using methyl 7-isatincarboxylate and 2-diisopropylaminoethyl chloride hydrochloride, a method analogous to that described in Reference Example 7 was carried out to obtain methyl 1-(2-diisopropylaminoethyl)-7-isatincarboxylate in an oil (yield: 94.6%).

IR (neat): νco 1720 cm⁻¹.

NMR (CDCl₃) δ: 0.80(12H, d, J=6.6 Hz), 2.51(2H, t, J=6.6 Hz), 2.95(2H, sept, J=6.6 Hz), 3.98(3H, s), 4.04(2H, t, J=6.6 Hz), 7.13(1H, t, J=7.7 Hz), 7.72(1H, dd, J=1.7 and 7.7 Hz), 7.86(1H, dd, J=1.7 and 7.7 Hz).

REFERENCE EXAMPLE 14

1-(2-Diisopropylaminoethyl)-5-methoxyisatin

To a solution of 3.00 g of 5-methoxyisatin and 3.39 g of 2-diisopropylaminoethyl chloride hydrochloride in 50 ml of dry N,N-dimethylformamide was added 1.36 g of sodium hydride (60% dispersion in mineral oil) with stirring under ice-cooling. The mixture was stirred for 1 hour at room temperature and then heated at 80° C. for 13 hours. The reaction mixture was concentrated under reduced pressure, and water was added to the residue. The mixture was extracted with ethyl acetate and the ethyl acetate layer was washed with water, dried over anhydrous magnesium sulfate and concentrated under reduced pressure. The residue was purified with silica gel flash column chromatography (eluent: chloroform) and recrystallized from hexane to obtain 3.33 g of 1-(2-diisopropylaminoethyl)-5-methoxyisatin having a melting point of 81°–82.5° C.

| | Elemental analysis as $C_{17}H_{24}N_2O_3$ | | |
|---|---|---|---|
| | C % | H % | N % |
| Calcd. | 67.08 | 7.95 | 9.20 |
| Found | 67.35 | 8.11 | 9.19 |

IR (KBr): νco 1715 cm⁻¹.

NMR (CDCl₃) δ: 0.97(12H, d, J=6.6 Hz), 2.68(2H, t, J=6.6 Hz), 3.03(2H, sept, J=6.6 Hz), 3.66(2H, t, J=6.6 Hz), 3.80(3H, s), 6.8–6.9(1H, m), 7.1–7.2(2H, m).

REFERENCE EXAMPLE 15

7-Bromo-1-(2-diisopropylaminoethyl)-5-methylisatin

To a suspension of 8.0 g of 5-methylisatin in 200 ml of acetic acid was added dropwise a solution of 3.3 ml of bromine in 50 ml of acetic acid with stirring at room temperature, and the mixture was heated at 50° C. for 16 hours. The reaction mixture was concentrated under reduced pressure, and the residue was recrystallized from methanol-hexane to obtain 11.4 g of 7-bromo-5-methylisatin having a melting point of 176°–180° C.

| | Elemental analysis as $C_9H_6BrNO_2$ | | |
|---|---|---|---|
| | C % | H % | N % |
| Calcd. | 45.03 | 2.52 | 5.83 |
| Found | 45.05 | 2.46 | 5.50 |

IR (KBr): νco 1730 cm⁻¹

NMR (d₆-DMSO) δ: 2.27(3H, s), 7.35(1H, s), 7.64(1H, s), 11.22(1H, s)

By using the 7-bromo-5-methylisatin and 2-diisopropylaminoethyl chloride hydrochloride, a method analogous to that described in Reference Example 1 was carried out to obtain 7-bromo-1-(2-diisopropylaminoethyl)-5-methylisatin having a melting point of 94°–97° C. (yield: 13.1%).

| | Elemental analysis as $C_{17}H_{23}BrN_2O_2$ | | |
|---|---|---|---|
| | C % | H % | N % |
| Calcd. | 55.59 | 6.31 | 7.63 |
| Found | 55.35 | 6.29 | 7.53 |

IR (KBr): νco 1730 cm$^{-1}$

NMR (CDCl$_3$) δ: 0.90(12H, d, J=6.6 Hz), 2.30(3H, s), 2.73(2H, t, J=6.6 Hz), 3.03(2H, sept, J=6.6 Hz), 4.17(2H, t, J=6.6 Hz), 7.37(1H, d, J=1.1 Hz), 7.52(1H, d, J=1.1 Hz).

REFERENCE EXAMPLE 16

1-(3-Diisopropylaminopropyl)-5-methylisatin

By using 5-methylisatin and 3-diisopropylaminopropyl chloride hydrochloride, a method analogous to that described in Reference Example 1 was carried out to obtain 1-(3-diisopropylaminopropyl)-5-methylisatin having a melting point of 87°–89° C. (yeld: 53.3%).

| Elemental analysis as C$_{18}$H$_{26}$N$_2$O$_2$ | | | |
|---|---|---|---|
|  | C % | H % | N % |
| Calcd. | 71.49 | 8.67 | 9.26 |
| Found | 71.61 | 8.86 | 9.24 |

IR (KBr): νco 1730 cm$^{-1}$.

NMR (CDCl$_3$) δ: 1.01(12H, d, J=6.1 Hz), 1.7–1.85(2H, m), 2.33(3H, s), 2.45–2.6(2H, m), 2.95–3.1(2H, m), 3.73(2H, t, J=7.1 Hz), 6.81(1H, d, J=7.7 Hz), 7.38(1H, d, J=7.7 Hz), 7.40(1H, s).

REFERENCE EXAMPLE 17

1-(2-Isopropylaminoethyl)isatin

A solution of 4.00 g of 1-(2-bromoethyl)isatin and 13.5 ml of isopropylamine in 160 ml of dry N,N-dimethylformamide was stirred for 1 hour at 80° C. The solution was concentrated under reduced pressure and the residue was dissolved in 50 ml of a 2N-hydrochloric acid. The solution was washed with ethyl acetate, neutralized by adding an aqueous sodium bicarbonate solution, and extracted with chloroform. The chloroform layer was washed with water, dried over anhydrous magnesium sulfate, and concentrated under reduced pressure. The residue was purified with silica gel column chromatography (eluent: chloroform/methanol=10/1) to obtain 3.11 g of 1-(2-isopropylaminoethyl)isatin in an oil.

| Elemental analysis as C$_{13}$H$_{16}$N$_2$O$_2$ | | | |
|---|---|---|---|
|  | C % | H % | N % |
| Calcd. | 67.22 | 6.94 | 12.06 |
| Found | 67.26 | 7.02 | 11.95 |

IR (neat): νNH 3300 cm$^{-1}$ νco 1725 cm$^{-1}$.

NMR (CDCl$_3$) δ: 1.05(6H, d, J=6.6 Hz), 1.50(1H, br-s), 2.86(1H, sept, J=6.6 Hz), 2.94(2H, t, J=6.6 Hz), 3.84(2H, t, J=6.6 Hz), 6.99(1H, d, J=7.7 Hz), 7.11(1H, t, J=7.7 Hz), 7.59(1H, t, J=7.7 Hz), 7.61(1H, d, J=7.7 Hz).

REFERENCE EXAMPLE 18

1-(2-tert-Butylaminoethyl)isatin

A solution of 3.00 g of 1-(2-bromoethyl)isatin, 12.6 ml of tert-butylamine and 1.80 g of sodium iodide in 100 ml of dry N,N-dimethylformamide was stirred for 1 hour at 110° C. The reaction mixture was concentrated under reduced pressure, and water was added to the residue. The mixture was extracted with ethyl acetate, and the ethyl acetate layer was washed with water, dried over anhydrous magnesium sulfate and concentrated under reduced pressure. The residue was purified with silica gel column chromatography (eluent: chloroform/methanol=10/1) and recrystallized from benzenehexane to obtain 1.36 g of 1-(2-trrt-butylaminoethyl)isatin having a melting point of 60°–62° C.

| Elemental analysis as C$_{14}$H$_{18}$N$_2$O$_2$ | | | |
|---|---|---|---|
|  | C % | H % | N % |
| Calcd. | 68.27 | 7.37 | 11.37 |
| Found | 68.22 | 7.40 | 11.19 |

IR (KBr): νNH 3290 cm$^{-1}$ νco 1720 cm$^{-1}$.

NMR (CDCl$_3$) δ: 1.07(9H, s), 1.50(1H, br), 2.89(2H, t, J=7.1 Hz), 3.81(2H, t, J=7.1 Hz), 7.00(1H, d, J=7.7 Hz), 7.11(1H, t, J=7.7 Hz), 7.58(1H, t, J=7.7 Hz), 7.60(1H, d, J=7.7 Hz).

REFERENCE EXAMPLE 19

1-[2-(N-Isopropylcyclohexylamino)ethyl]isatin

To a solution of 5.0 g of N-isopropylcyclohexylamine and 4.3 g of triethylamine in 100 ml of dry dichloromethane was added dropwise 5.8 g of acetoxyacetyl chloride with stirring under ice-cooling, and the mixture was stirred for 16 hours at room temperature. The reaction mixture was successively washed with an aqueous sodium bicarbonate solution and water, dried under reduced pressure to obtain 8.5 g of 2-acetoxy-N-cyclohexyl-N-isopropylacetamide in an oil.

IR (neat): νco 1735, 1650 cm$^{-1}$.

NMR (CDCl$_3$) δ: 1.05–1.9(16H, m), 2.18(3H, s), 2.3–2.5(1H, m), 3.1–3.15(1H, m), 4.67(2H, s).

4.1 Grams of lithium aluminum hydride was suspended in 500 ml of diethyl ether, and to the suspension was added dropwise 2.9 ml of concentrated sulfuric acid with stirring under ice-cooling and then the mixture was stirred for 1 hour under ice-cooling. To this reaction mixture was added dropwise a solution of 8.4 g of the above amido compound in 150 ml of diethyl ether with stirring under ice-cooling. The mixture was heated under reflux for 16 hours. The reaction mixture was cooled, and then to the cooled reaction mixture was successively added dropwise an aqueous sodium hydroxide solution and water with stirring under ice-cooling. The mixture was dried over anhydrous magnesium sulfate, and insoluble materials were filtered off. The filtrate was concentrated under reduced pressure to obtain 6.1 g of 2-(N-isopropylcyclohexylamino)ethanol in an oil.

IR (neat): νOH 3375 cm$^{-1}$.

NMR (CDCl$_3$) δ: 1.03(6H, d, J=6.6 Hz), 1.15–1.85(10H, m), 2.45–2.6(1H, m), 2.68(2H, t, J=5.5 Hz), 3.07(1H, sept, J=6.6 Hz), 3.25(1H, br-s), 3.45(2H, t, J=5.5 Hz).

6.0 Grams of the above alcohol compound obtained was dissolved in 100 ml of dry benzene, and to this solution was added dropwise 3.2 ml of thionyl chloride with stirring at room temperature. The mixture was heated under refulx for 4 hours. The reaction mixture was concentrated under reduced pressure, and the residue was triturated with diethyl ether. The precipitated crystals were collected by filtration to obtain 7.4 g of 2-(N-isopropylcyclohexylamino)ethyl chloride hydrochloride having a melting point of 99°–103° C.

| Elemental analysis as $C_{11}H_{23}Cl_2N$ | | | |
|---|---|---|---|
| | C % | H % | N % |
| Calcd. | 55.00 | 9.65 | 5.83 |
| Found | 54.82 | 10.00 | 5.73 |

NMR (CDCl$_3$) δ: 1.15–2.4(16H, m), 3.15–3.3(3H, m), 3.65–3.85(1H, m), 4.05–4.25(2H, m), 11.90(1H, br-s)

By using the 2-(N-isopropylcyclohexylamino)ethyl chloride hydrochloride obtained and isatin, a method analogous to that described in Reference Example 1 was carried out to obtain 1-[2-(N-isopropylcyclohexylamino)ethyl]isatin having a melting point of 103°–106° C (yield: 75.5%, recrystallizing solvent: ethyl acetatehexane).

| Elemental analysis as $C_{19}H_{26}N_2O_2$ | | | |
|---|---|---|---|
| | C % | H % | N % |
| Calcd. | 72.58 | 8.33 | 8.91 |
| Found | 72.37 | 8.48 | 8.99 |

IR (KBr): νco 1725 cm$^{-1}$.

NMR (CDCl$_3$) δ: 0.96(6H, d, J=6.6 Hz), 1.0–1.8(10H, m), 2.45–2.6(1H, m), 2.75(2H, t, J=6.6 Hz), 3.06(1H, sept, J=6.6 Hz), 3.68(2H, t, J=6.6 Hz), 6.91(1H, d, J=7.7 Hz), 7.08(1H, t, J=7.7 Hz), 7.57(1H, t, J=7.7 Hz), 7.58(1H, d, J=7.7 Hz).

REFERENCE EXAMPLE 20

1-[2-(N-Isopropylbenzylamino)ethyl]isatin

To a solution of 5.00 g of N-isopropylbenzylamine and 3.74 g of triethylamine in 60 ml of dry dichloromethane was added dropwise 3.84 g of chloroacetyl chloride with stirring under ice-cooling. The mixture was heated under reflux for 2 hours. After cooling, the reaction mixture was successively washed with water, a 10% hydrochloric acid and an aqueous sodium bicarbonate solution, dried over anhydrous magnesium sulfate and concentrated under reduced pressure to obtain 7.67 g of N-benzyl-2-chloro-N-isopropylacetamide in an oil.

IR (neat): νco 1640 cm$^{-1}$.

NMR (CDCl$_3$) δ: 1.15 and 1.21(6H, d, J=6.6 Hz), 3.91 and 4.19(2H, s), 4.23 and 4.78(1H, sept, J=6.6 Hz), 4.54(2H, s), 7.1–7.45(5H, m).

A solution of 7.66 g of the N-benzyl-2-chloro-N-isopropylacetamide in 20 ml of dry diethyl ether was added dropwise to a suspension of 1.29 g of lithium aluminum hydride in 300 ml of dry diethyl ether with stirring under ice-cooling, and the mixture was heated under reflux for 4 hours. After the reaction mixture was cooled, and to the cooled reaction mixture was added dropwise water with stirring under ice-cooling. Insoluble materials were filtered off. The filtrate was dried over anhydrous magnesium sulfate, and concentrated under reduced pressure. The residue was purified with silica gel column chromatography (eluent: chloroform) to obtain 3.61 g of 2-(N-isopropylbenzylamino)ethyl chloride in an oil.

NMR (CDCl$_3$) δ: 1.03(6H, d, J=6.6 Hz), 2.76(2H, t, J=7.1 Hz), 2.93(1H, sept, J=6.6 Hz), 3.32(2H, t, J=7.1 Hz), 3.62(2H, s), 7.2–7.45(5H, m).

By using isatin and the 2-(N-isopropylbenzylamino)ethyl chloride, a method analogous to that described in Reference Example 7 was carried out, and the reaction product was purified with silica gel column chromatography (eluent: chloroform) to obtain 1-[2-(N-isopropylbenzylamino)ethyl]isatin in an oil (yield: 43.4%).

| Elemental analysis as $C_{20}H_{22}N_2O_2$ | | | |
|---|---|---|---|
| | C % | H % | N % |
| Calcd. | 74.51 | 6.88 | 8.69 |
| Found | 74.57 | 6.81 | 8.57 |

IR (neat): νco 1730 cm$^{-1}$.

NMR (CDCl$_3$) δ: 1.06(6H, d, J=6.6 Hz), 2.68(2H, t, J=6.6 Hz), 3.07(1H, sept, J=6.6 Hz), 3.54(2H, s), 3.60(2H, t, J=6.6 Hz), 6.40(1H, d, J=7.7 Hz), 7.01(1H, t, J=7.7 Hz), 7.1–7.25(5H, m), 7.37(1H, dt, J=1.6 and 7.7 Hz), 7.50(1H, dd, J=1.6 and 7.7 Hz).

EXAMPLE 1

(E)-1-(2-Diisopropylaminoethyl)isatin 3-semicarbazone

A solution of 10.3 g of 1-(2-diisopropylaminoethyl)isatin, 5.1 g of semicarbazide hydrochloride and 3.7 g of sodium acetate in 150 ml of a mixture of ethanol and water (2:1) was stirred for 17 hours at room temperature. The yellow precipitates were collected by filtration and washed with aqueous ethanol. The filtrate and the washed the aqueous ethanol solution were combined and concentrated under reduced pressure. An aqueous sodium bicarbonate solution was added to the residue. The yellow precipitates were collected by filtration and washed with dichloromethane. The yellow precipitates were combined and recrystallized from aqueous methanol to obtain 9.3 g of (E)-1-(2-diisopropylaminoethyl)isatin 3-semicarbazone having a melting point of 193°–196° C.

| Elemental analysis as $C_{17}H_{25}N_5O_2$ | | | |
|---|---|---|---|
| | C % | H % | N % |
| Calcd. | 61.61 | 7.60 | 21.13 |
| Found | 61.52 | 7.67 | 21.00 |

IR (KBr): νNH 3380, 3320, 3180 cm$^{-1}$ νco 1680 cm$^{-1}$.

NMR (d$_6$-DMSO) δ: 0.89(12H, d, J=6.6 Hz), 2.60(2H, t, J=6.0 Hz), 2.99(2H, sept, J=6.6 Hz), 3.67(2H, t, J=6.0 Hz), 6.85(2H, br-s), 7.07(1H, t, J=7.1 Hz), 7.08(1H, d, J=7.1 Hz), 7.43(1H, t, J=7.1 Hz), 8.08(1H, d, J=7.1 Hz), 10.21(1H, s).

EXAMPLE 2

(E)-1-(2-Diisopropylaminoethyl)isatin 3-(4-methylsemicarbazone)

To a solution of 1.37 g of 1-(2-diisopropylaminoethyl)isatin and 0.49 g of 4-methylsemicarbazide in ml of a mixture of ethanol and water (2:1) was added 3 drops of acetic acid, and then the mixture was heated at 60° C. for 6 hours. The yellow precipitates were collected by filtration and recrystallized from aqueous ethanol to obtain 0.86 g of (E)-1-(2-diisopropylaminoethyl)isatin 3-(4-methylsemicarbazone) having a melting point of 175°–177° C.

| Elemental analysis as $C_{18}H_{27}N_5O_2 \cdot \frac{1}{2}H_2O$ | | | |
|---|---|---|---|
| | C % | H % | N % |
| Calcd. | 61.52 | 7.94 | 19.93 |

-continued

| Elemental analysis as $C_{18}H_{27}N_5O_2 \cdot \frac{1}{2}H_2O$ | | | |
|---|---|---|---|
| | C % | H % | N % |
| Found | 61.56 | 8.09 | 19.71 |

IR (KBr): $\nu$NH 3475, 3300, 3200, 3120 cm$^{-1}$ $\nu$co 1690 cm$^{-1}$.

NMR (d$_6$-DMSO) $\delta$: 0.88(12H, d, J=6.6 Hz), 2.61(2H, t, J=5.8 Hz), 2.76(3H, d, J=4.4 Hz), 2.99(2H, sept, J=6.6 Hz), 3.68(2H, t, J=5.8 Hz), 7.06(1H, t, J=7.3 Hz), 7.07(1H, d, J=7.3 Hz), 7.18(1H, q, J=4.4 Hz), 7.42(1H, t, J=7.3 Hz), 8.08(1H, d, J=7.3 Hz), 10.30(1H, s).

EXAMPLE 3

(E)-1-(2-Diisopropylaminoethyl)isatin 3-(4-phenylsemicarbazone)

To a solution of 1.37 g of 1-(2-diisopropylaminoethyl)isatin and 0.86 g of 4-phenylsemicarbazide in ml of a mixture of ethanol and water (2:1) was added 3 drops of acetic acid, and the mixture was stirred for 3 hours at 70° C. The yellow precipitates were collected by filtration, and recrystallized from ethanol to obtain 1.24 g of (E)-1-(2-diisopropylaminoethyl)isatin 3-(4-phenylsemicarbazone) having a melting point of 157°–159° C.

| Elemental analysis as $C_{23}H_{29}N_5O_2$ | | | |
|---|---|---|---|
| | C % | H % | N % |
| Calcd. | 67.79 | 7.17 | 17.19 |
| Found | 67.53 | 7.25 | 17.24 |

IR (KBr): $\nu$NH 3240, 3110 cm$^{-1}$ $\nu$co 1680 cm$^{-1}$.

NMR (d$_6$-DMSO) $\delta$: 0.90(12H, d, J=6.6 Hz), 2.62(2H, t, J=6.6 Hz), 3.00(2H, sept, J=6.6 Hz), 3.70(2H, t, J=6.6 Hz), 7.0–7.7(8H, m), 8.12(1H, d, J=7.7 Hz), 9.49(1H, s), 10.44(1H, s).

EXAMPLE 4

(E)-1-(2-Diisopropylaminoethyl)isatin 3-(4-cyclohexylsemicarbazone)

To a suspension of 0.91 g of 1-(2-diisopropylaminoethyl)isatin and 1.00 g of 4-cyclohexylsemicarbazide hydrochloride in 17 ml of a mixture of ethanol and water (2:1) was added 0.42 g of sodium acetate, and the mixture was stirred for 17 hours at room temperature. The reaction mixture was concentrated under reduced pressure, and an aqueous sodium bicarbonate solution was added to the residue. The precipitates were collected by filtration, washed with water, and recrystallized from aqueous ethanol to obtain 0.99 g of (E)-1-(2-diisopropylaminoethyl)isatin 3-(4-cyclohexylsemicarbazone) having a melting point of 164°–166° C.

| Elemental analysis as $C_{23}H_{35}N_5O_2$ | | | |
|---|---|---|---|
| | C % | H % | N % |
| Calcd. | 66.80 | 8.53 | 16.93 |
| Found | 66.85 | 8.56 | 16.89 |

IR (KBr): $\nu$NH 3260, 3160 cm$^{-1}$ $\nu$co 1680, 1660 cm$^{-1}$.

NMR (d$_6$-DMSO) $\delta$: 0.89(12H, d, J=6.6 Hz), 1.1–2.0(10H, m), 2.60(2H, t, J=6.1 Hz), 2.99(2H, sept, J=6.6 Hz), 3.5–3.65(1H, m), 3.67(2H, t, J=6.1 Hz), 7.0–7.15(3H, m), 7.43(1H, t, J=7.7 Hz), 8.07(1H, d, J=7.7 Hz), 10.21(1H, s).

EXAMPLE 5

(E)-1-(2-Diisopropylaminoethyl)isatin 3-(4-benzylsemicarbazone)

To a suspension of 1.37 g of 1-(2-diisopropylaminoethyl)isatin and 1.20 g of 4-benzylsemicarbazide hydrochloride in 20 ml of a mixture of ethanol and water (2:1) was added 0.50 g of sodium acetate. The mixture was stirred for 18 hours at room temperature, and then concentrated under reduced pressure. An aqueous sodium bicarbonate solution was added to the residue. The precipitates were collected by filtration, washed with water, and recrystallized from aqueous ethanol to obtain 1.21 g of (E)-1-(2-diisopropylaminoethyl)isatin 3-(4-benzylsemicarbazone) having a melting point of 164°–165° C.

| Elemental analysis as $C_{24}H_{31}N_5O_2$ | | | |
|---|---|---|---|
| | C % | H % | N % |
| Calcd. | 68.38 | 7.41 | 16.61 |
| Found | 68.37 | 7.60 | 16.59 |

IR (KBr): $\nu$NH 3400, 3220 cm$^{-1}$ $\nu$co 1710, 1680 cm$^{-1}$.

NMR (d$_6$-DMSO) $\delta$: 0.88(12H, d, J=6.6 Hz), 2.60(2H, t, J=6.6 Hz), 2.99(2H, sept, J=6.6 Hz), 3.67(2H, t, J=6.6 Hz), 4.42(2H, d, J=6.0 Hz), 7.0–7.5(8H, m), 7.78(1H, t, J=6.0 Hz), 8.09(1H, d, J=7.7 Hz), 10.35(1H, s).

(E)-1-(2-Diisopropylaminoethyl)isatin 3-(4-benzylsemicarbazone)

A suspension of 137 mg of 1-(2-diisopropylaminoethyl)isatin and 120 mg of 4-benzylsemicarbazide hydrochloride in 2 ml of a mixture of ethanol and water (2:1) was stirred for 11 hours at room temperature, and an aqueous sodium bicarbonate solution was added to the reaction mixture. The precipitates were collected by filtration, washed with water and recrystallized from aqueous ethanol to obtain 147 mg of (E)-1-(2-diisopropylaminoethyl)isatin 3-(4-benzylsemicarbazone). Chemical properties of the product were identical with those of the product obtained by Example 5.

EXAMPLE 7

(Z)-1-(2-Diisopropylaminoethyl)isatin 3-(4-isopentylsemicarbazone)

A suspension of 1.10 g of (E)-1-(2-diisopropylaminoethyl)isatin 3-semicarbazone and 0.29 g of isopentylamine in a mixture of 150 ml of dry toluene and 20 ml of dry N,N-dimethylformamide was stirred for 23 hours at 120° C. The reaction mixture was concentrated under reduced pressure, and the residue was dissolved in dichloromethane. The solution was washed with water, dried over anhydrous magnesium sulfate and concentrated under reduced pressure. The residue was purified with silica gel flash column chromatography (eluent: chloroform) to obtain 1.12 g of (Z)-1-(2-diisopropylaminoethyl)isatin 3-(4-isopentylsemicarbazone) in a viscous oil.

| Elemental analysis as $C_{22}H_{35}N_5O_2 \cdot 0.8H_2O$ | | | |
|---|---|---|---|
| | C % | H % | N % |
| Calcd. | 63.52 | 8.87 | 16.84 |
| Found | 63.61 | 8.72 | 16.64 |

IR (neat): $\nu$NH 3300, 3250 cm$^{-1}$ $\nu$co 1700, 1670 cm$^{-1}$.

NMR (CDCl$_3$) δ: 0.96(6H, d, J=6.6 Hz), 0.98(12H, d, J=6.6 Hz), 1.52(2H, q, J=7.1 Hz), 1.6-1.85(1H, m), 2.67(2H, t, J=7.1 Hz), 3.03(2H, sept, J=6.6 Hz), 3.41(2H, dt, J=6.0 and 7.1 Hz), 3.71(2H, t, J=7.1 Hz), 6.32(1H, t, J=6.0 Hz), 6.90(1H, d, J=7.7 Hz), 7.08(1H, t, J=7.7 Hz), 7.34(1H, t, J=7.7 Hz), 7.56(1H, d, J=7.7 Hz), 11.94(1H, s).

EXAMPLE 8

(Z)-1-(2-Diisopropylaminoethyl)isatin 3-semicarbazone 1.10 Grams of (E)-1-(2-diisopropylaminoethyl)isatin 3-semicarbazone was suspended in a mixture of ml of dry toluene and 20 ml of dry N,N-dimethylformamide, and the suspension was stirred for 3 hours at 120° C. The reaction mixture was concentrated under reduced pressure, and the residue was dissolved in dichloromethane. The solution was washed with water, dried over anhydrous magnesium sulfate, and concentrated under reduced pressure. The residue was recrystallized from benzene-hexane to obtain 0.84 g of (Z)-1-(2-diisopropylaminoethyl)isatin 3-semicarbazone having a melting point of 189°-191° C.

| Elemental analysis as $C_{17}H_{25}N_5O_2$ | | | |
|---|---|---|---|
| | C % | H % | N % |
| Calcd. | 61.61 | 7.60 | 21.13 |
| Found | 61.61 | 7.61 | 20.88 |

IR (KBr): $\nu$NH 3450, 3200 cm$^{-1}$ $\nu$co 1710, 1670 cm$^{-1}$.

NMR (d$_6$-DMSO) δ: 0.86(12H, d, J=6.6 Hz), 2.64(2H, t, J=6.6 Hz), 2.98(2H, sept, J=6.6 Hz), 3.72(2H, t, J=6.6 Hz), 7.05-7.25(4H, m), 7.40(1H, t, J=7.1 Hz), 7.63(1H, d, J=7.1 Hz), 11.73(1H, s).

EXAMPLE 9

(E)-1-(2-Diisopropylaminoethyl)isatin 3-semicarbazone hydrochloride

To a suspension of 4.97 g of (E)-1-(2-diisopropylaminoethyl)isatin 3-semicarbazone in 370 ml of methanol was added 15.0 ml of a 1N-hydrochloric acid to make a solution. The solution was concentrated under reduced pressure, and diethyl ether was added to the residue. The precipitates were collected by filtration and recrystallized from ethanol to obtain 5.37 g of (E)-1-(2-diisopropylaminoethyl)isatin 3-semicarbazone hydrochloride having a melting point of 255°-25° C. (decomposition).

| Elemental analysis as $C_{17}H_{26}ClN_5O_2 \cdot 0.5H_2O$ | | | |
|---|---|---|---|
| | C % | H % | N % |
| Calcd. | 54.18 | 7.22 | 18.58 |
| Found | 54.10 | 7.40 | 18.39 |

IR (KBr): $\nu$NH 3470, 3350, 3240 cm$^{-1}$ $\nu$co 1700 cm$^{-1}$.

NMR (d$_6$-DMSO) δ: 1.2-1.5(12H, m), 3.15-3.45(2H, m), 3.6-3.8(2H, m), 4.1-4.3(2H, m), 6.99(2H, s), 7.14(1H, t, J=7.7 Hz), 7.23(1H, d, J=7.7 Hz), 7.47(1H, t, J=7.7 Hz), 8.25(1H, d, J=7.7 Hz), 10.11(1H, br-s), 10.41(1H, s).

EXAMPLE 10

(E)-1-(2-Diisopropylaminoethyl)isatin 3-semicarbazone

A suspension of 10.00 g of 1-(2-diisopropylaminoethyl)isatin and 4.88 g of semicarbazide hydrochloride in 350 ml of a mixture of ethanol and water (2.5:1) was stirred for 2 hours at room temperature. The suspension was warmed to make a solution, and then 44.0 ml of a 1N-aqueous sodium hydroxide solution was added dropwise to the solution. The precipitates were collected by filtration and washed with water to obtain 10.56 g of (E)-1-(2-diisopropylaminoethyl)isatin 3-semicarbazone. The chemical properties of this product were identical with those of the product obtained by Examle 1.

EXAMPLE 11

(E)-1-(3-Diisopropylaminopropyl)isatin 3-semicarbazone

By using 1-(3-diisopropylaminopropyl)isatin and semicarbazide hydrochloride, a method analogous to that described in Example 4 was carried out to obtain (E)-1-(3-diisopropylaminopropyl)isatin 3-semicarbazone having a melting point of 173°-175° C. (yield: 66.6%, recrystallizing solvent: methanol-benzene).

| Elemental analysis as $C_{18}H_{27}N_5O_2$ | | | |
|---|---|---|---|
| | C % | H % | N % |
| Calcd. | 62.59 | 7.88 | 20.27 |
| Found | 62.31 | 7.96 | 20.13 |

IR (KBr): $\nu$NH 3400, 3300, 3175 cm$^{-1}$ $\nu$co 1680 cm$^{-1}$.

NMR (d$_6$-DMSO) δ: 0.94(12H, d, J=6.6 Hz), 1.64(2H, quint, J=6.6 Hz), 2.46(2H, t, J=6.6 Hz), 2.96(2H, sept, J=6.6 Hz), 3.72(2H, t, J=6.6 Hz), 6.90(2H, br-s), 7.09(1H, t, J=7.7 Hz), 7.10(1H, d, J=7.7 Hz), 7.43(1H, t, J=7.7 Hz), 8.12(1H, d, J=7.7 Hz), 10.25(1H, br-s).

EXAMPLE 12

(E)-1-(2-Diisopropylamino-1-methylethyl)isatin 3-semicarbazone

By using 1-(2-diisopropylamino-1-methylethyl)isatin and semicarbazide hydrochloride, a method analogous to that described in Example 10 was carried out and the reaction product was recrystallized from ethanol to obtain (E)-1-(2-diisopropylamino-1-methylethyl)isatin 3-semicarbazone having a melting point of 195°-197° C. (yield: 65.3%).

| Elemental analysis as $C_{18}H_{27}N_5O_2$ | | | |
|---|---|---|---|
| | C % | H % | N % |
| Calcd. | 62.59 | 7.88 | 20.27 |
| Found | 62.71 | 7.95 | 20.14 |

IR (KBr): $\nu$NH 3300, 3180 cm$^{-1}$ $\nu$co 1680 cm$^{-1}$.

NMR (d$_6$-DMSO) δ: 0.73(6H, d, J=6.6 Hz), 0.91(6H, d, J=6.6 Hz), 1.41(3H, d, J=7.1 Hz), 2.61(1H, dd,

J=5.0 and 14.3 Hz), 2.85–3.05(3H, m), 4.25–4.5(1H, m), 6.82(2H, br-s), 7.04(1H, t, J=7.7 Hz), 7.20(1H, d, J=7.7 Hz), 7.38(1H, t, J=7.7 Hz), 8.08(1H, d, J=7.7 Hz), 10.18(1H, s).

EXAMPLE 13

(E)-1-(2-Diisopropylaminopropyl)isatin 3-semicarbazone

By using 1-(2-diisopropylaminopropyl)isatin and semicarbazide hydrochloride, a method analogous to that described in Example 10 was carried out, and the reaction product was recrystallized from ethanol to obtain (E)-1-(2-diisopropylaminopropyl)isatin 3-semicarbazone having a melting point of 201°–204° C. (yield: 77.6%).

| Elemental analysis as $C_{18}H_{27}N_5O_2$ | | | |
|---|---|---|---|
| | C % | H % | N % |
| Calcd. | 62.59 | 7.88 | 20.27 |
| Found | 62.78 | 7.97 | 19.96 |

IR (KBr): $\nu$NH 3400, 3300 cm$^{-1}$ $\nu$co 1680 cm$^{-1}$.

NMR (d$_6$-DMSO) δ: 0.78(6H, d, J=6.6 Hz), 0.96(6H, d, J=6.6 Hz), 1.05(3H, d, J=6.6 Hz), 3.12(2H, sept, J=6.6 Hz), 3.25–3.35(1H, m), 3.37(1H, dd, J=6.0 and 13.2 Hz), 3.75(1H, dd, J=8.2 and 13.2 Hz), 6.83(2H, br-s), 7.06(1H, t, J=7.2 Hz), 7.10(1H, d, J=7.2 Hz), 7.41(1H, t, J=7.2 Hz), 8.09(1H, d, J=7.2 Hz), 10.19(1H, s).

EXAMPLE 14

(E)-1-(2-Diisopropylaminoethyl)-5-methylisatin 3-semicarbazone

By using 1-(2-diisopropylaminoethyl)-5-methylisatin and semicarbazide hydrochloride, a method analogous to that described in Example 4 was carried out to obtain (E)-1-(2-diisopropylaminoethyl)-5-methylisatin 3-semicarbazone having a melting point of 159°–161° C. (yield: 53.9%, recrystallizing solvent: chloroform-hexane).

| Elemental analysis as $C_{18}H_{27}N_5O_2 \cdot 0.3H_2O$ | | | |
|---|---|---|---|
| | C % | H % | N % |
| Calcd. | 61.62 | 7.93 | 19.96 |
| Found | 61.59 | 7.88 | 19.95 |

IR (KBr): $\nu$NH 3450, 3380, 3250 cm$^{-1}$ $\nu$co 1695 cm$^{-1}$.

NMR (d$_6$-DMSO) δ: 0.89(12H, d, J=6.6 Hz), 2.32(3H, s), 2.5–2.65(2H, m), 2.9–3.05(2H, m), 3.55–3.7(2H, m), 6.86(2H, br-s), 6.96(1H, d, J=7.7 Hz), 7.24(1H, d, J=7.7 Hz), 7.99(1H, s), 10.19(1H, s).

EXAMPLE 15

(E)-1-(2-Diisopropylaminoethyl)-5-methylisatin 3-(4-benzylsemicarbazone)

By using 1-(2-diisopropylaminoethyl)-5-methylisatin and 4-benzylsemicarbazide hydrochloride, a method analogous to that described in Example 6 was carried out to obtain (E)-1-(2-diisopropylaminoethyl)5-methylisatin 3-(4-benzylsemicarbazone) having a melting point of 159°–160° C. (yield: 74.6%, recrystallizing solvent: ethanol).

| Elemental analysis as $C_{25}H_{33}N_5O_2$ | | | |
|---|---|---|---|
| | C % | H % | N % |
| Calcd. | 68.94 | 7.64 | 16.08 |
| Found | 68.87 | 7.79 | 16.00 |

IR (KBr): $\nu$NH 3340, 3180 cm$^{-1}$ $\nu$co 1695, 1680 cm$^{-1}$.

NMR (d$_6$-DMSO) δ: 0.88(12H, d, J=6.6 Hz), 2.31(3H, s), 2.58(2H, t, J=6.6 Hz), 2.98(2H, sept, J=6.6 Hz), 3.64(2H, t, J=6.6 Hz), 4.42(2H, d, J=6.0 Hz), 6.96(1H, d, J=8.2 Hz), 7.2–7.4(6H, m), 7.77(1H, t, J=6.0 Hz), 7.98(1H, s), 10.33(1H, s).

EXAMPLE 16

(E)-1-(2-Diisopropylaminoethyl)-5-methylisatin 3-(4-methylsemicarbazone)

To a solution of 1.00 g of 1-(2-diisopropylaminoethyl)-5-methylisatin and 0.34 g of 4-methylsemicarbazide in 15 ml of a mixture of ethanol and water (2:1) was added 3.8 ml of a 1N-hydrochloric acid. The mixture was stirred for 16 hours at room temperature. To the reaction mixture was added an aqueous sodium bicarbonate solution, and the mixture was extracted with chloroform. The chloroform layer was washed with water, dried over anhydrous magnesium sulfate, and concentrated under reduced pressure. The residue was recrystallized from ethanol to obtain 0.77 g of (E)-1-(2-diisopropylaminoethyl)-5-methylisatin 3-(4-methylsemicarbazone) having a melting point of 157.5°–158.5° C.

| Elemental analysis as $C_{19}H_{29}N_5O_2 \cdot 0.2H_2O$ | | | |
|---|---|---|---|
| | C % | H % | N % |
| Calcd. | 62.85 | 8.16 | 19.29 |
| Found | 62.82 | 8.28 | 19.10 |

IR (KBr): $\nu$NH 3340, 3200 cm$^{-1}$ $\nu$co 1685 cm$^{-1}$.

NMR (d$_6$-DMSO) δ: 0.88(12H, d, J=6.6 Hz), 2.31(3H, s), 2.59(2H, t, J=6.6 Hz), 2.77(3H, d, J=4.4 Hz), 2.98(2H, sept, J=6.6 Hz), 3.64(2H, d, J=6.6 Hz), 6.95(1H, d, J=7.7 Hz), 7.17(1H, q, J=4.4 Hz), 7.23(1H, d, J=7.7 Hz), 7.99(1H, s), 10.26(1H, s).

EXAMPLE 17

(E)-1-(2-Diisopropylaminoethyl)-7-methylisatin 3-semicarbazone

By using 1-(2-diisopropylaminoethyl)-7-methylisatin and semicarbazide hydrochloride, a method analogous to that described in Example 4 was carried out to obtain (E)-1-(2-diisopropylaminoethyl)-7-methylisatin 3-semicarbazone having a melting point of 194°–195° C. (yield: 75.7%).

| Elemental analysis as $C_{18}H_{27}N_5O_2$ | | | |
|---|---|---|---|
| | C % | H % | N % |
| Calcd. | 62.59 | 7.88 | 20.27 |
| Found | 62.39 | 7.92 | 19.95 |

IR (KBr): $\nu$NH 3480, 3360, 3290 cm$^{-1}$ $\nu$co 1710 cm$^{-1}$.

NMR (d$_6$-DMSO) δ: 0.90(12H, d, J=6.6 Hz), 2.53(3H, s), 2.58(2H, t, J=6.6 Hz), 2.99(2H, sept, J=6.6 Hz), 3.91(2H, t, J=6.6 Hz), 6.85(2H, br-s), 6.99(1H, t, J=7.7 Hz), 7.20(1H, d, J=7.7 Hz), 7.95(1H, d, J=7.7 Hz), 10.19(1H, s).

EXAMPLE 18

(E)-1-(2-Diisopropylaminoethyl)-5-fluoroisatin 3-semicarbazone

By using 1-(2-diisopropylaminoethyl)-5-fluoroisatin and semicarbazide hydrochloride, a method analogous to that described in Example 6 was carried out to obtain (E)-1-(2-diisopropylaminoethyl)-5-fluoroisatin 3-semicarbazone having a melting point of 158°–160° C. (yield: 86.5%, recrystallizing solvent: chloroform-hexane).

| Elemental analysis as $C_{17}H_{24}FN_5O_2$ | | | |
|---|---|---|---|
| | C % | H % | N % |
| Calcd. | 58.44 | 6.92 | 20.04 |
| Found | 58.22 | 7.11 | 19.85 |

IR (KBr): $\nu$NH 3460, 3400, 3250 cm$^{-1}$ $\nu$co 1715 cm$^{-1}$.

NMR (d$_6$-DMSO) δ: 0.88(12H, d, J=6.6 Hz), 2.60(2H, t, J=6.6 Hz), 2.99(2H, sept, J=6.6 Hz), 3.68(2H, t, J=6.6 Hz), 6.90(2H, br-s), 7.08(1H, dd, J=4.4 and 8.8 Hz), 7.28(1H, dt, J=2.2 and 8.8 Hz), 8.11(1H, dd, J=2.2 and 8.8 Hz), 10.42(1H, s).

EXAMPLE 19

(E)-5-Chloro-1-(2-diisopropylaminoethyl)isatin 3-semicarbazone

By using 5-chloro-1-(2-diisopropylaminoethyl)isatin and semicarbazide hydrochloride, a method analogous to that described in Example 4 was carried out to obtain (E)-5-chloro-1-(2-diisopropylaminoethyl)isatin 3-semicarbazone having a melting point of 154°–155° C. (yield: 49.4%, recrystallizing solvent: chloroform-hexane).

| Elemental analysis as $C_{17}H_{24}ClN_5O_2 \cdot 0.05CHCl_3$ | | | |
|---|---|---|---|
| | C % | H % | N % |
| Calcd. | 55.08 | 6.52 | 18.83 |
| Found | 54.82 | 6.64 | 18.94 |

IR (KBr): $\nu$NH 3450, 3400, 3250 cm$^{-1}$ $\nu$co 1710, 1695 cm$^{-1}$.

NMR (d$_6$-DMSO) δ: 0.87(12H, d, J=6.6 Hz), 2.60(2H, t, J=6.6 Hz), 2.98(2H, sept, J=6.6 Hz), 3.68(2H, t, J=6.6 Hz), 6.90(2H, br-s), 7.10(1H, d, J=8.8 Hz), 7.47(1H, dd, J=1.6 and 8.8 Hz), 8.28(1H, d, J=1.6 Hz), 10.50(1H, s).

EXAMPLE 20

(E)-6-Chloro-1-(2-diisopropylaminoethyl)isatin 3-semicarbazone

By using 6-chloro-1-(2-diisopropylaminoethyl)isatin and semicarbazide hydrochloride, a method analogous to that described in Example 4 was carried out to obtain (E)-6-chloro-1-(2-diisopropylaminoethyl)isatin 3-semicarbazone having a melting point of 205°–208° C. (yield: 69.4%, recrystallizing solvent: aqueous methanol).

| Elemental analysis as $C_{17}H_{24}ClN_5O_2$ | | | |
|---|---|---|---|
| | C % | H % | N % |
| Calcd. | 55.81 | 6.61 | 19.14 |
| Found | 55.93 | 6.70 | 19.16 |

IR (KBr): $\nu$NH 3400, 3300, 3180 cm$^{-1}$ $\nu$co 1685 cm$^{-1}$.

NMR (d$_6$-DMSO) δ: 0.86(12H, d, J=6.0 Hz), 2.61(2H, t, J=6.0 Hz), 2.99(2H, sept, J=6.0 Hz), 3.70(2H, t, J=6.0 Hz), 6.85(2H, br-s), 7.11(1H, dd, J=1.7 and 8.2 Hz), 7.21(1H, d, J=1.7 Hz), 8.09(1H, d, J=8.2 Hz), 10.35(1H, br).

EXAMPLE 21

(E)-5-Bromo-1-(2-diisopropylaminoethyl)isatin 3-semicarbazone

By using 5-bromo-1-(2-diisopropylaminoethyl)isatin and semicarbazide hydrochloride, a method analogous to that described in Example 4 was carried out to obtain (E)-5-bromo-1-(2-diisopropylaminoethyl)isatin 3-semicarbazone having a melting point of 149°–153° C. (yield: 72.6%, recrystallizing solvent: chloroform-hexane).

| Elemental analysis as $C_{17}H_{24}BrN_5O_2$ | | | |
|---|---|---|---|
| | C % | H % | N % |
| Calcd. | 49.76 | 5.90 | 17.07 |
| Found | 49.79 | 6.01 | 16.99 |

IR (KBr): $\nu$NH 3460, 3250 cm$^{-1}$ $\nu$co 1710, 1690 cm$^{-1}$.

NMR (d$_6$-DMSO) δ: 0.87(12H, d, J=6.6 Hz), 2.59(2H, t, J=6.6 Hz), 2.98(2H, sept, J=6.6 Hz), 3.67(2H, t, J=6.6 Hz), 6.88(2H, br-s), 7.05(1H, d, J=8.8 Hz), 7.59(1H, dd, J=1.7 and 8.8 Hz), 8.38(1H, d, J=1.7 Hz), 10.52(1H, s).

EXAMPLE 22

(E)-5-Bromo-1-(2-diisopropylaminoethyl)isatin 3-(4-cyclohexylsemicarbazone)

By using 5-bromo-1-(2-diisopropylaminoethyl)isatin and 4-cyclohexylsemicarbazide, a method analogous to that described in Example 16 was carried out to obtain (E)-5-bromo-1-(2-diisopropylaminoethyl)isatin 3-(4-cyclohexylsemicarbazone) having a melting point of 155°–156° C. (yield: 89.9%, recrystallizing solvent: chloroform-hexane).

| Elemental analysis as $C_{23}H_{34}BrN_5O_2$ | | | |
|---|---|---|---|
| | C % | H % | N % |
| Calcd. | 56.10 | 6.96 | 14.22 |
| Found | 56.11 | 7.11 | 14.09 |

IR (KBr): $\nu$NH 3200 cm$^{-1}$ $\nu$co 1690 cm$^{-1}$.

NMR (d$_6$-DMSO) δ: 0.88(12H, d, J=6.6 Hz), 1.05–1.95(10H, m), 2.59(2H, t, J=6.6 Hz), 2.98(2H, sept, J=6.6 Hz), 3.5–3.75(3H, m), 7.0–7.15(2H, m), 7.59(1H, d, J=8.2 Hz), 8.35(1H, d, J=1.6 Hz), 10.50(1H, br-s).

EXAMPLE 23

(E)-5-Acetamido-1-(2-diisopropylaminoethyl)isatin 3-semicarbazone

By using 5-acetamido-1-(2-diisopropylaminoethyl)isatin and semicarbazide hydrochloride, a method analogous to that described in Example 4 was carried out, and the reaction product was purified with silica gel column chromatography (eluent: chloroform/methanol=50/1) and then recrystallized from chloroform-hexane to obtain (E)-5-acetamido-1-(2-diisopropylaminoethyl)isatin 3-semicarbazone having a melting point of 135°–137° C. (yield: 32.0%).

| Elemental analysis as $C_{19}H_{28}N_6O_3 \cdot 0.05CHCl_3$ | | | |
|---|---|---|---|
| | C % | H % | N % |
| Calcd. | 58.01 | 7.17 | 21.31 |
| Found | 58.03 | 7.35 | 21.45 |

IR (KBr): $\nu$NH 3250 cm$^{-1}$ $\nu$co 1690 cm$^{-1}$.

NMR (d$_6$-DMSO) δ: 0.89(12H, d, J=6.6 Hz), 2.03(3H, s), 2.60(2H, t, J=6.6 Hz), 2.99(2H, sept, J=6.6 Hz), 3.65(2H, t, J=6.6 Hz), 6.86(2H, br-s), 7.00(1H, d, J=8.2 Hz), 7.64(1H, dd, J=1.6 and 8.2 Hz), 8.09(1H, d, J=1.6 Hz), 9.89(1H, s), 10.07(1H, s).

EXAMPLE 24

(E)-5-Amino-1-(2-diisopropylaminoethyl)isatin 3-semicarbazone

By using 5-amino-1-(2-diisopropylaminoethyl)isatin and semicarbazide hydrochloride, a method analogous to that described in Example 4 was carried out to obtain (E)-5-amino-1-(2-diisopropylaminoethyl)isatin 3-semicarbazone having a melting point of 221°–222° C. (decomposition) (yield: 74.0%, recrystallizing solvent: chloroform-methanol).

| Elemental analysis as $C_{17}H_{26}N_6O_2$ | | | |
|---|---|---|---|
| | C % | H % | N % |
| Calcd. | 58.94 | 7.56 | 24.26 |
| Found | 58.86 | 7.70 | 24.26 |

IR (KBr): $\nu$NH 3290 cm$^{-1}$ $\nu$co 1690, 1670 cm$^{-1}$.

NMR (d$_6$-DMSO) δ: 0.90(12H, d, J=6.6 Hz), 2.56(2H, t, J=6.6 Hz), 2.98(2H, sept, J=6.6 Hz), 3.57(2H, t, J=6.6 Hz), 4.84(2H, br-s), 6.66(1H, dd, J=1.8 and 8.5 Hz), 6.76(1H, d, J=8.5 Hz), 6.82(2H, br-s), 7.35(1H, d, J=1.8 Hz), 9.80(1H, s).

EXAMPLE 25

(Z)-1-(2-Diisopropylaminoethyl)-7-methoxycarbonylisatin 3-semicarbazone

By using methyl 1-(2-diisopropylaminoethyl)-7-isatincarboxylate and semicarbazide hydrochloride, a method analogous to that described in Example 6 was carried out, and the reaction product was purified with silica gel column chromatography (eluent: chloroform/ethanol=20/1) and then recrystallized from chloroform-hexane to obtain (Z)-1-(2-diisopropylaminoethyl)-7-methoxycarbonylisatin 3-semicarbazone having a melting point of 192°–195° C. (yield: 28.1%).

| Elemental analysis as $C_{19}H_{27}N_5O_4 \cdot 0.05CHCl_3$ | | | |
|---|---|---|---|
| | C % | H % | N % |
| Calcd. | 57.86 | 6.90 | 17.71 |
| Found | 57.98 | 7.06 | 17.42 |

IR (KBr): $\nu$NH 3450, 3200 cm$^{-1}$ $\nu$co 1715, 1685 cm$^{-1}$.

NMR (d$_6$-DMSO) δ: 0.73(12H, d, J=6.6 Hz), 2.43(2H, t, J=6.6 Hz), 2.88(2H, sept, J=6.6 Hz), 3.91(3H, s), 3.94(2H, t, J=6.6 Hz), 7.22(1H, t, J=7.7 Hz), 7.26(2H, br-s), 7.65(1H, d, J=7.7 Hz), 7.87(1H, d, J=7.7 Hz), 11.69(1H, s).

EXAMPLE 26

(E)-1-(2-Diisopropylaminoethyl)-5-methoxyisatin 3-semicarbazone

By using 1-(2-diisopropylaminoethyl)-5-methoxyisatin and semicarbazide hydrochloride, a method analogous to that described in Example 6 was carried out to obtain (E)-1-(2-diisopropylaminoethyl)-5-methoxyisatin 3-semicarbazone having a melting point of 157°–159° C. (yield: 84.0%, recrystallizing solvent: ethanol).

| Elemental analysis as $C_{18}H_{27}N_5O_3 \cdot 0.4C_2H_5OH$ | | | |
|---|---|---|---|
| | C % | H % | N % |
| Calcd. | 59.44 | 7.80 | 18.44 |
| Found | 59.16 | 7.97 | 18.21 |

IR (KBr): $\nu$NH 3400 cm$^{-1}$ $\nu$co 1680 cm$^{-1}$.

NMR (d$_6$-DMSO) δ: 0.89(12H, d, J=6.6 Hz), 2.58(2H, t, J=6.6 Hz), 2.98(2H, sept, J=6.6 Hz), 3.63(2H, t, J=6.6 Hz), 3.80(3H, s), 6.85(2H, br-s), 6.97(1H, d, J=8.8 Hz), 7.02(1H, dd, J=2.2 and 8.8 Hz), 7.76(1H, d, J=2.2 Hz), 10.42(1H, s).

EXAMPLE 27

(E)-7-Bromo-1-(2-diisopropylaminoethyl)-5-methylisatin 3-semicarbazone

By using 7-bromo-1-(2-diisopropylaminoethyl)-5-methylisatin and semicarbazide hydrochloride, a method analogous to that described in Example 4 was carried out to obtain (E)-7-bromo-1-(2-diisopropylaminoethyl)-5-methylisatin 3-semicarbazone having a melting point of 189°–192° C. (yield: 87.9%, recrystallizing solvent: chloroform-hexane)

| Elemental analysis as $C_{18}H_{26}BrN_5O_2$ | | | |
|---|---|---|---|
| | C % | H % | N % |
| Calcd. | 50.95 | 6.18 | 16.50 |
| Found | 50.66 | 6.30 | 16.20 |

IR (KBr): $\nu$NH 3450 cm$^{-1}$ $\nu$co 1695 cm$^{-1}$.

NMR (d$_6$-DMSO) δ: 0.87(12H, d, J=6.6 Hz), 2.29(3H, s), 2.55-2.7(2H, m), 2.9-3.05(2H, m), 4.0-4.15(2H, m), 6.90(2H, br), 7.42(1H, s), 8.04(1H, s), 10.39(1H, br-s).

EXAMPLE 28

(E)-1-(3-Diisopropylaminopropyl)-5-methylisatin 3-semicarbazone

By using 1-(3-diisopropylaminopropyl)-5-methylisatin and semicarbazide hydrochloride, a method analogous to that described in Example 4 was carried out to obtain (E)-1-(3-diisopropylaminopropyl)-5-methylisatin 3-semicarbazone having a melting point of 145°–148° C. (yield: 72.2%).

| Elemental analysis as $C_{19}H_{29}N_5O_2.0.3H_2O$ | | | |
|---|---|---|---|
| | C % | H % | N % |
| Calcd. | 62.54 | 8.18 | 19.19 |
| Found | 62.42 | 8.32 | 19.01 |

IR (KBr): $\nu$NH 3380 cm$^{-1}$ $\nu$co 1695 cm$^{-1}$.

NMR (d$_6$-DMSO) δ: 0.94(12H, d, J=6.6 Hz), 1.62(2H, quint, J=7.1 Hz), 2.32(3H, s), 2.45(2H, t, J=7.1 Hz), 2.96(2H, sept, J=6.6 Hz), 3.68(2H, t, J=7.1 Hz), 6.83(2H, br-s), 6.97(1H, d, J=7.7 Hz), 7.24(1H, d, J=7.7 Hz), 8.01(1H, s), 10.19(1H, s).

EXAMPLE 29

(E)-1-(2-Isopropylaminoethyl)isatin 3-semicarbazone

By using 1-(2-isopropylaminoethyl)isatin and semicarbazide hydrochloride, a method analogous to that described in Example 10 was carried out, and the reaction product was recrystallized from ethanol to obtain (E)-1-(2-isopropylaminoethyl)isatin 3-semicarbazone having a melting point of 169°–172° C. (decomposition) (yield: 49.8%).

| Elemental analysis as $C_{14}H_{19}N_5O_2$ | | | |
|---|---|---|---|
| | C % | H % | N % |
| Calcd. | 58.12 | 6.62 | 24.20 |
| Found | 57.98 | 6.62 | 24.03 |

IR (KBr): $\nu$NH 3400, 3310, 3180 cm$^{-1}$ $\nu$co 1685 cm$^{-1}$.

NMR (d$_6$-DMSO) δ: 0.94(6H, d, J=6.0 Hz), 2.65–2.85(3H, m), 3.77(2H, t, J=6.6 Hz), 6.83(2H, br-s), 7.07(1H, t, J=7.7 Hz), 7.14(1H, d, J=7.7 Hz), 7.40(1H, t, J=7.7 Hz), 8.10(1H, d, J=7.7 Hz).

EXAMPLE 30

(E)-1-(2-tert-Butylaminoethyl)isatin 3-semicarbazone

By using 1-(2-tert-butylaminoethyl)isatin and semicarbazide hydrochloride, a method analogous to that described in Example 10 was carried out, and the reaction product was recrystallized from ethanol to obtain (E)-1-(2-tert-butylaminoethyl)isatin 3-semicarbazone having a melting point of 173°–176° C. (decomposition) (yield: 40.3%).

| Elemental analysis as $C_{15}H_{21}N_5O_2$ | | | |
|---|---|---|---|
| | C % | H % | N % |
| Calcd. | 59.39 | 6.98 | 23.09 |
| Found | 59.18 | 6.96 | 23.14 |

IR (KBr): $\nu$NH 3375, 3300, 3170 cm$^{-1}$ $\nu$co 1680 cm$^{-1}$.

NMR (d$_6$-DMSO) δ: 0.98(9H, s), 2.71(2H, t, J=6.9 Hz), 3.74(2H, t, J=6.9 Hz), 6.84(2H, br-s), 7.07(1H, t, J=7.7 Hz), 7.14(1H, d, J=7.7 Hz), 7.41(1H, t, J=7.7 Hz), 8.10(1H, d, J=7.7 Hz)

EXAMPLE 31

(E)-1-[2-(N-Isopropylcyclohexylamino)ethyl]isatin 3-semicarbazone

By using 1-[2-(N-isopropylcyclohexylamino)ethyl]isatin and semicarbazide hydrochloride, a method analogous to that described in Example 6 was carried out to obtain (E)-1-[2-(N-isopropylcyclohexylamino)isatin 3-semicarbazone having a melting point of 181°–184° C. (yield: 82.9%, recrystallizing solvent: aqueous methanol).

| Elemental analysis as $C_{20}H_{29}N_5O_2$ | | | |
|---|---|---|---|
| | C % | H % | N % |
| Calcd. | 64.67 | 7.87 | 18.85 |
| Found | 64.52 | 7.94 | 18.54 |

IR (KBr): $\nu$NH 3375, 3320, 3180 cm$^{-1}$ $\nu$co 1680 cm$^{-1}$.

NMR (d$_6$-DMSO) δ: 0.87(6H, d, J=6.6 Hz), 0.95–1.75(10H, m), 2.4–2.55(1H, m), 2.66(2H, t, J=6.6 Hz), 3.03(1H, sept, J=6.6 Hz), 3.66(2H, t, J=6.6 Hz), 6.86(2H, br-s), 7.0–7.15(2H, m), 7.42(1H, t, J=7.7 Hz), 8.09(1H, d, J=7.7 Hz), 10.21(1H, s).

EXAMPLE 32

(E)-1-[2-(N-Isopropylbenzylamino)ethyl]isatin 3-semicarbazone

By using 1-[2-(N-isopropylbenzylamino)ethyl]isatin and semicarbazide hydrochloride, a method analogous to that described in Example 6 was carried out to obtain (E)-1-[2-(N-isopropylbenzylamino)ethyl]isatin 3-semicarbazone having a melting point of 193°–194° C. (yield: 52.7%, recrystallizing solvent: ethanol).

| Elemental analysis as $C_{21}H_{25}N_5O_2$ | | | |
|---|---|---|---|
| | C % | H % | N % |
| Calcd. | 66.47 | 6.64 | 18.46 |
| Found | 66.42 | 6.67 | 18.51 |

IR (KBr): $\nu$NH 3380, 3320, 3180 cm$^{-1}$ $\nu$co 1685 cm$^{-1}$.

NMR (d$_6$-DMSO) δ: 1.02(6H, d, J=6.6 Hz), 2.71(2H, t, J=6.0 Hz), 3.04(1H, sept, J=6.6 Hz), 3.68(2H, s), 3.81(2H, t, J=6.0 Hz), 6.95(1H, d, J=7.7 Hz), 7.00(2H, br-s), 7.16(1H, t, J=7.7 Hz), 7.2–7.35(5H, m), 7.42(1H, t, J=7.7 Hz), 8.19(1H, d, J=7.7 Hz), 10.32(1H, s).

What is claimed is:

1. A method for prophylaxis and treatment of an ulcer disease in a mammalian digestive tract which comprises dosage adminstration to the mammal of an isatin compound corresponding to the formula:

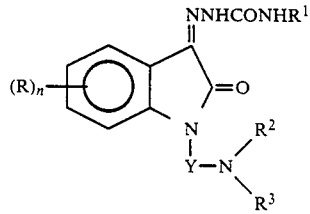

where $R^1$ is hydrogen or a $C_1$–$C_6$ alkyl, $C_6$–$C_{10}$ aryl, $C_7$–$C_{10}$ aralkyl or $C_3$–$C_6$ cycloalkyl group, $R^2$ is a $C_3$-$C_6$ branched-chain alkyl group, $R^3$ is hydrogen or a $C_1$-$C_6$ alkyl, $C_7$-$C_{10}$ aralkyl or $C_3$-$C_6$ cycloalkyl group, R is halogen or a $C_1$-$C_6$ alkyl, $C_1$-$C_6$ alkoxy, amino, $C_1$-$C_5$ acylamino or $C_2$-$C_7$ alkoxycarbonyl group, n is an integer of 0-2, and Y is a $C_2$-$C_4$ alkylene group; or a pharmaceutically acceptable salt thereof.

2. A method in accordance with claim 1 wherein the isatin compound corresponds to formula:

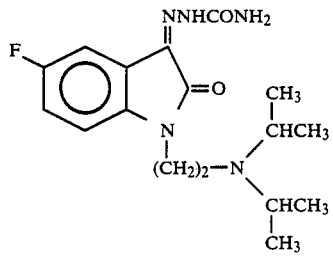

or a pharmaceutically acceptable salt thereof.

3. A method in accordance with claim 1 wherein the isatin compound corresponds to the formula:

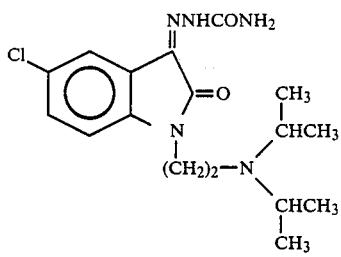

or a pharmaceutically acceptable salt thereof.

4. A method in accordance with claim 1 wherein the isatin compound corresponds to the formula:

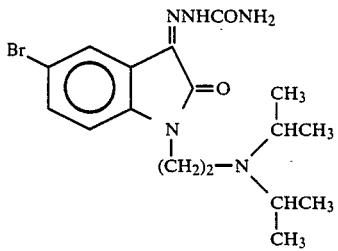

or a pharmaceutically acceptable salt thereof.

5. A method in accordance with claim 1 wherein the isatin compound corresponds to the formula:

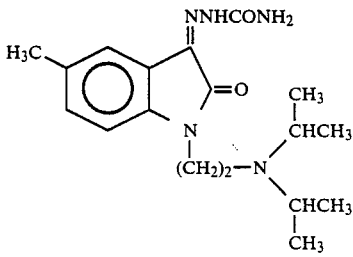

or a pharmaceutically acceptable salt thereof.

6. A method in accordance with claim 1 wherein the isatin compound corresponds to the formula:

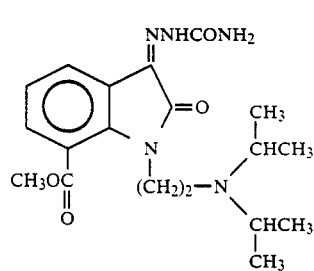

or a pharmaceutically acceptable salt thereof.

7. A method in accordance with claim 1 wherein the isatin compound corresponds to the formula:

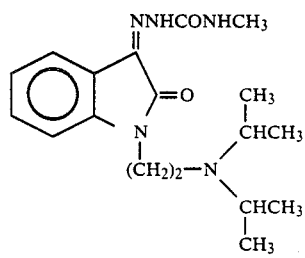

or a pharmaceutically acceptable salt thereof.

8. A method in accordance with claim 1 wherein the isatin compound corresponds to the formula:

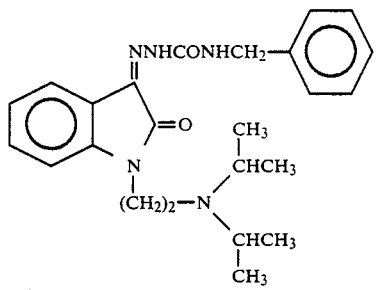

or a pharmaceutically acceptable salt thereof.

9. A method in accordance with claim 1 wherein the isatin compound corresponds to the formula:

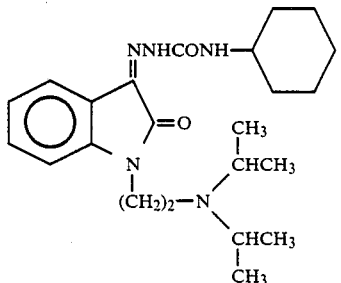

or a pharmaceutically acceptable salt thereof.

10. A method in accordance with claim 1 wherein the isatin compound corresponds to the formula:

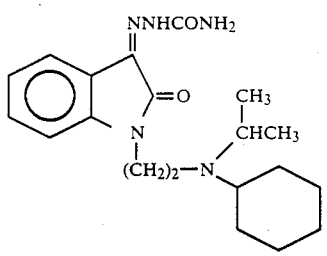
or a pharmaceutically acceptable salt thereof.
11. A method in accordance with claim 1 wherein the isatin compound corresponds to the formula:
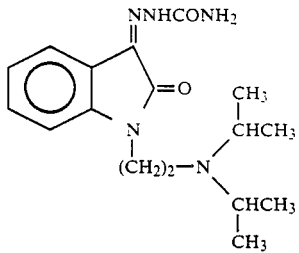
or a pharmaceutically acceptable salt thereof.

UNITED STATES PATENT AND TRADEMARK OFFICE
CERTIFICATE OF CORRECTION

PATENT NO. : 4,780,477
DATED : October 25, 1988
INVENTOR(S) : Kobayashi et al

It is certified that error appears in the above-identified patent and that said Letters Patent is hereby corrected as shown below:

Col. 2, line 56, "or mammals" should be --of mammals--

Col. 3, line 45, "propylactic", should be --prophylactic--

Column 14, line 2, "1-(2-trrt-butylaminoethyl)isatin" should be --1-(2-tert-butylaminoethyl)isatin--.

Column 14, line 27, after "dried", insert --over anhydrous magnesium sulfate and concentrated--.

Column 14, line 62, "refulx" should be --reflux--

Column 16, line 55, before "ml", insert --20--.

Column 17, line 20, before "ml", insert --20--.

Column 19, line 21, before "ml", insert --150--.

Column 19, line 58, "255°-25°C" should be --255°-259°C--.

Column 20, line 21, "Examle" should be --Example--.

UNITED STATES PATENT AND TRADEMARK OFFICE
CERTIFICATE OF CORRECTION

PATENT NO. : 4,780,477
DATED : October 25, 1988
INVENTOR(S) : Kobayashi, et. al.

It is certified that error appears in the above-indentified patent and that said Letters Patent is hereby corrected as shown below:

Column 25, line 53, delete "C".

Signed and Sealed this

First Day of February, 1994

Attest:

BRUCE LEHMAN

Attesting Officer     Commissioner of Patents and Trademarks